and novel 2,5-bis(benzyloxy)tetrahydrofu-

United States Patent [19]
Eggensperger et al.

[11] 4,004,024
[45] Jan. 18, 1977

[54] DISINFECTANT FURANS

[75] Inventors: Heinz Eggensperger; Wolfgang Beilfuss; Helmut Hermann Ehlers, all of Hamburg, Germany

[73] Assignee: Sterling Drug Inc., New York, N.Y.

[22] Filed: July 7, 1975

[21] Appl. No.: 593,558

[30] Foreign Application Priority Data
July 15, 1974 Germany .................. 2433836

[52] U.S. Cl. ............................. 424/285
[51] Int. Cl.² .......................... A61K 31/34
[58] Field of Search .................. 424/285

[56] References Cited
OTHER PUBLICATIONS
Pershin et al. – Chem. Abst. vol. 62, (1965) p. 15284e.

*Primary Examiner*—Sam Rosen
*Attorney, Agent, or Firm*—Frederik W. Stonner; B. Woodrow Wyatt

[57] ABSTRACT

There is disclosed a method for controlling bacteria, fungi and spores which comprises applying thereto a bactericidally, fungicidally and sporicidally effective amount of a furan selected from 2-($R_1$O)-5-($R_2$O)-2,5-dihydrofuran and 2-($R_1$O)-5-($R_2$O)-tetrahydrofuran or mixtures thereof; a process for preparing a 2,5-bis(-$R_1$O)-2,5-tetrahydrofuran and 2,5-bis($R_1$O)-tetrahydrofuran; and novel 2,5-bis(benzyloxy)tetrahydrofuran.

10 Claims, No Drawings

DISINFECTANT FURANS

BACKGROUND OF THE INVENTION

1. Field of the Invention

The invention relates to a method for controlling bacteria, fungi and spores (sporulating bacteria) which comprises applying thereto a 2-($OR_1$)-5-($OR_2$)-di(or tetra)hydrofuran, to a process for the preparation of said furans, and to a novel furan.

2. Description of the Prior Art

Chemicals as well as physical procedures are suitable for disinfection and sterilization of objects such as surgical instruments. For example, physical procedures, such as heatand steam sterilization, and the use of ionizing radiation or ultrasonics have proved to be of practical use. However, their general applicability is limited by several factors, such as the need for expensive equipment and skilled personnel, and danger inherent in improper use.

Chemical disinfection and sterilization procedures have the advantage that they are more generally applicable and less expensive than physical procedures. However, a marked disadvantage of many known chemical processes is the toxicity to man of the active ingredients employed. For example, ethylene oxide is a toxic agent and β-propiolactone is known to have carcinogenic effects. Of the less toxic classes of chemical substances, many are suitable for use as disinfecting agents because they possess good bactericidal properties, but few are known which combine sporicidal activity with environmental compatibility.

Some aldehydes are known which are bactericidal as well as sporicidal; among these are formaldehyde, glyoxal, glutardialdehyde, and other saturated dialdehydes (cf. DT-OS No. 1,492,326). The use of these aldehydes for the purpose of disinfection and sterilization, however, is fraught with disadvantages: formaldehydes in the required concentration has a disagreeable poignant odor; glyoxal has insufficient bactericidal activity; glutaraldehyde and other saturated dialdehydes have a disagreeable poignant odor, and exhibit sporicidal activity only in a mildly alkaline environment in which they are not stable over longer periods of time.

A number of compounds belonging to the class of 2-($OR_1$)-5-($OR_2$)-di(or tetra)hydrofurans employed in the method of this invention are described in the literature, e.g., where $R_1$ and $R_2$ are identical and are methyl, ethyl, n-propyl, isopropyl, n-butyl, isopentyl, cyclohexyl and allyl in the case of dihydrofuran, and methyl, ethyl and allyl in the case of tetrahydrofuran. However, the prior art does not teach that the dihydrofurans and tetrahydrofurans employed in the method of this invention possess bactericidal, fungicidal and sporicidal activity.

SUMMARY OF THE INVENTION

In a method aspect of the invention there is provided a method for controlling bacteria, fungi and spores which comprises applying thereto a bactericidally, fungicidally and sporicidally effective amount of a furan selected from the group consisting of 2-($R_1O$)-5-($R_2O$)-2,5-dihydrofuran (I) and 2-($R_1O$)-5-($R_2O$)-tetrahydrofuran (II), or mixtures of said compounds, where $R_1$ and $R_2$ independently are selected from the group consisting of alkyl having from one to twelve carbon atoms, alkyl having from one to twelve carbon atoms substituted by from one to three of the same or different halo substituents, hydroxyalkyl having from two to twelve carbon atoms, nitroalkyl having from two to twelve carbon atoms, phenylalkyl wherein alkyl has from one to two carbon atoms, phenoxyalkyl wherein alkyl has from one to two carbon atoms, cycloalkyl having from five to six ring carbon atoms and a total of from five to twelve carbon atoms, alkenyl having from three to four carbon atoms, alkynyl having from three to four carbon atoms, glycidyl, alkoxyalkyl having from three to twelve carbon atoms and alkoxyalkoxyalkyl having from four to twelve carbon atoms; where in each case phenyl and phenoxy are unsubstituted or substituted by one or two of the same or different substituents selected from the group consisting of halo, hydroxy and nitro.

In a process aspect of the invention there is provided a process for preparing a furan selected from the group consisting of 2,5-bis($R_1O$)-2,5-dihydrofuran and 2,5-bis($R_1O$)tetrahydrofuran which comprises reacting a compound selected from the group consisting of 2,5-bis(RO)-2,5-dihyrofuran and 2,5-bis(RO)tetrahydrofuran with about two moles of an alcohol of the formula $R_1OH$, where R is alkyl having from one to four carbon atoms, and $R_1$ has the same meaning defined hereinabove, provided R and $R_1$ are not identical, in the presence of an acid-catalyst at a temperature of from about 60° to about 200° C.

DETAILED DESCRIPTION INCLUSIVE OF THE PREFERRED EMBODIMENTS

The furans I and II employed in the method of the invention can be prepared by well-known process and/or by a novel process which is a separate aspect of this invention as disclosed hereinabove.

Known procedures include the reaction of furan with bromine in the presence of an excess of the appropriate alcohol [J. Amer. Chem. Soc. 72, 869 (1952)]. The tetrahydrofuran derivatives are obtained by catalytic hydrogenation of the corresponding dihydrofuran derivatives [J. Amer. Chem. Soc 72, 869 (1952)] or by ozonolysis of 1,5,9-cyclododecatriene, in presence of the appropriate alcohol and subsequent catalytic hydrogenation of the formed ozonide (Ja-Ps No. 71/19930).

In the novel process of the invention, certain of the furans I and II are prepared by reaction of a 2,5-bis(-RO)-2,5-dihydrofuran or 2,5-bis(RO)tetrahydrofuran, where R has the meaning hereinbefore defined, with about one mole of alcohol $R_1OH$ or about two moles of alcohol $R_1OH$, where $R_1$ has the meaning defined hereinbefore, in the presence of a strong acidcatalyst at elevated temperatures. When about one mole of alcohol $R_1OH$ is employed, the unsymmetrical 2-($R_1O$)-5-(RO)-2,5-dihydrofuran or 2-($R_1O$)-5-(RO)tetrahydrofuran is obtained, and when about two moles of alcohol $R_1OH$ is employed the symmetrical 2,5-bis(-$R_1O$)-2,5-dihydrofuran or 2,5-bis($R_1O$)tetrahydrofuran is obtained. To ensure that the reaction proceeds to completion the alcohol ROH which is formed during the reaction is removed by distillation. The reactions proceed according to the following scheme:

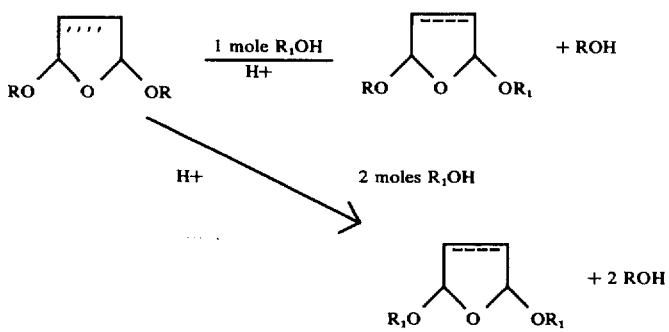

The reaction can be carried out neat or in the presence of a solvent. Suitable solvents are polar and nonpolar aprotic solvents, having a boiling point higher than that of the alcohol ROH to be removed from the reaction mixture. Such solvents are, for example, benzene, toluene, dioxane, acetonitrile and dimethylformamide.

A wide variety of acids can be employed as catalysts in the reaction. For example, acids which are conveniently employed are p-toluenesulfonic acid, glacial acetic acid and strongly acidic ion exchange resins in the $H^+$-form.

The reaction time is dependent on the reaction temperature and reactivity of the alcohol $R_1OH$ employed. Generally the time of reaction is about 30 minutes to six hours at reaction temperatures of about 80° to about 110° C. Reaction times of about one to about two hours are preferred.

The reaction temperature may vary within wide limits, e.g., from about 60° to about 120° C. The reaction products can be isolated by crystallization or distillation using standard procedures.

Preferred furans used as intermediates in the process of the invention are 2,5-bis(methoxy)-2,5-dihydrofuran and 2,5-bis(methoxy)tetrahydrofuran.

The method of the invention has wide applicability in many fields of technology which are affected adversely due to contamination by bacteria, fungi and spores. However, a preferred application is the field of disinfection and sterilization of inanimate surfaces, particularly cold sterilization of instruments, equipment and thermolabile plastics such as are used in hospitals and medical practice. For such latter applications a pleasing odor is desirable and good water solubility is important, both of which properties are possessed by the furans employed in the method of the invention. The degree of water solubility of such furans is dependent on the nature of the $R_1$ and $R_2$ substituents and is particularly good where $R_1$ and $R_2$ are lower-alkyl or oxygen containing substituents. The odor of the furans I and II is faint and pleasantly fruit-ether like, and, when employed in concentrations of 2 weight percent or less, the odor, if noticeable at all, is pleasant.

In practicing the method of the invention, the furans I and II can be formulated as dilute solutions in aqueous or alcoholic media, which, if desired, additionally may contain surfactants, anticorrosive agents, conventional carriers and adjuvants, and also other disinfecting agents which additionally may be sporicidally effective. For example, in preparing compositions for practicing the method of the invention there can be employed the following:

1. Water
2. Primary, secondary or tertiary mono- or polyvalent aliphatic/alcohols whereby the alcohol can be replaced in part by water, for example, methanol, ethanol, n-propanol, ethylene glycol and glycerine.
3. Mono- and dialdehydes, such as formaldehyde, glyoxal and glutaraldehyde.
4. Nonionic, anionic, cationic and amphoteric surfactants.
5. Antimicrobially active organic acids such as lactic, citric and formic acids.
6. Specially substituted phenols such as 2,6-dimethyl-4-bromophenol.
7. Thiocyanates such as sodium-, potassium-, or ammonium thiocyanate.
8. Anticorrosive agents such as phosphates, borates, silicates, and benzoates, further 1,2,3-benzotriazole, 2-mercaptobenzoxazole.

In utilizing the foregoing described formulations for disinfecting surfaces, they can be applied by conventional means such as spraying, swabbing and immersion. The formulations can also be formulated for use as aerosol sprays and foams.

While the efficacy of the furans I and II persists at high dilutions, in practicing the method of the invention the furans I and II are preferably employed in concentrations of 0.1 to 1 weight percent as bactericides and fungicides, and 0.1 to 4 weight percent, more preferably 2 weight percent, as sporicides.

Throughout the specification it will be understood that alkyl and alkoxy can be straight or branched; and that halo represents chloro, bromo, iodo and fluoro.

Preferred furans I and II in practicing the method of the invention are those where $R_1$ and $R_2$ are identical and are sec-butyl, tert.-butyl, n-pentyl, n-hexyl, n-heptyl, n-octyl, n-decyl, n-dodecyl, neopentyl, 2-ethylhexyl, benzyl, 2-phenethyl, cyclohexyl, trimethylcyclohexyl, cyclopentyl, glycidyl, 2-phenoxyethyl, 2-chloroethyl, 2-bromoethyl, 1,3-dichloropropyl, 2,3-dibromopropyl, 2,2,2-trichloroethyl, 2-methoxyethyl, 2-ethoxyethyl, 2-propoxyethyl, 2-($\beta$-ethoxyethoxy)-ethyl, 2-hydroxyethyl, 3,5-dichlorobenzyl, allyl, and propargyl; particularly preferred are 2,5-bis(methoxy)-2,5-dihydrofuran (hereinafter BMO-DHF) and 2,5-bis(methoxy)tetrahydrofuran (hereinafter BMO-THF).

The invention is illustrated by the following examples without, however, being limited thereto.

EXAMPLE 1

Preparation of 2,5-bis(benzyloxy)tetrahydrofuran 0.3 mole 2,5-BMO-THF and 0.6 mole benzyl alcohol were heated to 80° to 90° C. for 1 hour in the presence of 10 mg p-toluenesulfonic acid and the liberated methanol was distilled off. The residue was washed with water, taken up in chloroform and dried over $Na_2SO_4$. Subsequent fractional distillation yielded the title compound as a pale yellow somewhat viscous oil of pleasant odor; b.p. 60° C. (1 mm). Yield 71%.

EXAMPLE 2

Preparation of 2,5-bis(allyloxy)tetrahydrofuran 0.2 mole 2,5-BMO-THF and 0.4 mole allyl alcohol were heated for 90 minutes to 95° C. in the presence of 3 ml glacial acetic acid during which time the liberated methanol was distilled off. Fractional distillation yielded the title compound as a clear colorless oil, b.p. 70° C. (3 mm). Yield 60%.

EXAMPLE 3

The sporicidal activity of compositions employed in practicing the method of the invention was determined in the organism carrier test in accordance with the Richtlinien fur die Prufung chemischer Disinfektionsmittel der Deutschen Gesellschaft fur Hygiene und Mikrobiologie (3. Auflage, 1972). The tests were carried out against the following spores: *Bacillus megaterium*, *Bacillus mesentericus*, and *Bacillus subtilis*. Table 1 lists the results of these tests for five compositions (I–V) used in practicing the method of the invention and, for comparison, also for two compositions (IIa and Va) containing the known disinfectant glutaraldehyde as the only active ingredient.

Table I

| Composition | | Kill Time In Hours | | |
|---|---|---|---|---|
| | | B. megaterium | B. mesentericus | B. subtilis |
| I. | BMO-THF 3% | | | |
| | Isopropanol 0.5% | | | |
| | Emulsifier* 0.1% | | | |
| | Phosphoric acid | 1 | 2 | 4 |
| | Methyl ester 0.05% | | | |
| | Water q.s. ad 100 | | | |
| II. | BMO-THF 2% | | | |
| | Glutaraldehyde 1% | | | |
| | Emulsifier* 0.1% | | | |
| | Phosphoric acid | 1 | 1 | 4 |
| | Methyl ester 0.02% | | | |
| | Water q.s. ad 100 | | | |
| IIa. | Glutaraldehyde 1% | | | |
| | Emulsifier* 0.1% | | | |
| | Phosphoric acid | 2 | 2 | >6 |
| | Methyl ester 0.2% | | | |
| | Water q.s. ad 100 | | | |
| III. | BMO-THF 1.5% | | | |
| | Formalin 1.5% | | | |
| | Isopropanol 1.5% | | | |
| | Emulsifier* 0.1% | | | |
| | Phosphoric acid | 2 | 1 | 4 |
| | Methyl ester 0.05% | | | |
| | Water q.s. ad 100 | | | |
| IV. | BMO-THF 1.6% | | | |
| | Formalin 1.6% | | | |
| | Emulsifier* 0.1% | | | |
| | Phosphoric acid | 1 | 1 | 2 |
| | Methyl ester 0.05% | | | |
| | Water q.s. ad 100 | | | |
| V. | BMO-THF 3% | | | |
| | Water q.s. ad 100 | 1 | 1 | 4 |
| Va. | Glutaraldehyde 3% | | | |
| | Water q.s. ad 100 | 1 | 1 | 4 |

*1 part ethoxylated oxo-alcohol and 1 part disodium monolaurethsulfosuccinate

EXAMPLE 4

The bactericidal and fungicidal activities of compositions employed in practicing the method of the invention was determined in a suspension test in accordance with the Richtlinien fur die Prufung chemischer Disinfektionsmittel der Deutschen Gesellschaft fur Hygiene and Mikrobiologie (3. Auflage, 1972). The tests were carried out against the following organisms:

Bacteria

*Staphylococcus aureus*
*Escherichia coli*
*Pseudomonas aeroginosa*
*Proteus*

Fungi

*Trichophyton mentagrophytes*
*Microsporum gypseum*
*Candida albicans*

Table 2 lists the results of these tests for six compositions (VI–XI) used in the practicing method of the invention.

Table 2

| Composition | | Kill Time In Minutes | | | | | | |
|---|---|---|---|---|---|---|---|---|
| | | S. aureus | E. Coli | Pseu. aeroginosa | Proteus | T. mentagrophytes | M. gypseum | C. albicans |
| VI. | BMO-THF 1% | | | | | | | |
| | Betaine 3% | 2.5 | 15 | 2.5 | 5 | 2.5 | 2.5 | 15 |
| | Water q.s. ad 100 | | | | | | | |
| VII. | BMO-THF 0.5% | | | | | | | |
| | Betaine 1.5% | 5 | 15 | 5 | 5 | 2.5 | 2.5 | 15 |
| | Water q.s. ad 100 | | | | | | | |
| VIII. | BMO-THF 0.25% | | | | | | | |

Table 2-continued

| Composition | | Kill Time In Minutes | | | | | | |
|---|---|---|---|---|---|---|---|---|
| | | S. aureus | E. Coli | Pseu. aeroginosa | Proteus | T. mentagrophytes | M. gypseum | C. albicans |
| Betaine | 0.75% | 15 | 30 | 15 | 15 | 15 | 5 | 30 |
| Water q.s. ad | 100 | | | | | | | |
| IX. BMO-DHF | 0.5% | | | | | | | |
| Water q.s. ad | 100 | 5 | 15 | 15 | 15 | 2.5 | 5 | 30 |
| X. 2,5-Bis(ethoxy)-tetrahydrofuran | 1% | 5 | 5 | 15 | 15 | | | |
| Water q.s. ad | 100 | | | | | | | |
| XI. BMO-THF | 1% | | | | | | | |
| Potassium thiocyanate | 1% | 2.5 | 2.5 | 2.5 | 2.5 | | | |
| Water ad | a 100 | | | | | | | |

We claim:

1. A method for controlling bacteria, fungi and spores which comprises applying thereto a bactericidally, fungicidally and sporicidally effective amount of a furan selected from the group consisting of 2-($R_1O$)-5-($R_2O$)-2,5-dihydrofuran and 2-($R_1O$)-5-($R_2O$)-tetrahydrofuran, or mixtures of said compounds, where $R_1$ and $R_2$ independently are selected from the group consisting of alkyl having from one to twelve carbon atoms, alkyl having from one to twelve carbon atoms substituted by from one to three of the same or different halo substituents, hydroxyalkyl having from two to twelve carbon atoms, nitroalkyl having from two to twelve carbon atoms, phenylalkyl wherein alkyl has from one to two carbon atoms, phenoxyalkyl wherein alkyl has from one to two carbon atoms, cycloalkyl having from five to six ring carbon atoms and a total of from five to twelve carbon atoms, alkenyl having from three to four carbon atoms, alkynyl having from three to four carbon atoms, glycidyl, alkoxyalkyl having from three to twelve carbon atoms and alkoxyalkoxyalkyl having from four to twelve carbon atoms; where in each case phenyl and phenoxy are unsubstituted or substituted by one or two of the same or different substituents selected from the group consisting of halo, hydroxy and nitro.

2. A method according to claim 1 where $R_1$ and $R_2$ are identical.

3. A method according to claim 2 where $R_1$ and $R_2$ are selected from the group consisting of methyl, ethyl, benzyl and allyl.

4. A method according to claim 3 where the furan is 2-($R_1O$)-5-($R_2O$)-tetrahydrofuran and $R_1$ and $R_2$ are benzyl or allyl.

5. A method according to claim 3 where $R_1$ and $R_2$ are methyl or ethyl.

6. A method according to claim 5 where the furan is 2-($R_1O$)-5-($R_2O$)-tetrahydrofuran.

7. A method according to claim 6 where the furan is 2,5-bis(methoxy)tetrahydrofuran.

8. A method according to claim 6 where the furan is 2,5-bis(ethoxy)tetrahydrofuran.

9. A method according to claim 5 where the furan is 2-($R_1O$)-5-($R_2O$)-2,5dihydrofuran.

10. A method according to claim 9 where the furan is 2,5-bis(methoxy)-2,5-dihydrofuran.

* * * * *